(12) United States Patent
Veasey et al.

(10) Patent No.: US 10,226,579 B2
(45) Date of Patent: *Mar. 12, 2019

(54) DRIVE MECHANISMS SUITABLE FOR USE IN DRUG DELIVERY DEVICES

(71) Applicant: Sanofi-Aventis Deutschland GMBH, Frankfurt am Main (DE)

(72) Inventors: Robert Frederick Veasey, Warwickshire (GB); Christopher Nigel Langley, Warwickshire (GB); Steven Wimpenny, Warwickshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 66 days.

This patent is subject to a terminal disclaimer.

(21) Appl. No.: 15/352,893

(22) Filed: Nov. 16, 2016

(65) Prior Publication Data

US 2017/0056598 A1 Mar. 2, 2017

Related U.S. Application Data

(63) Continuation of application No. 14/504,016, filed on Oct. 1, 2014, now Pat. No. 9,526,843, which is a (Continued)

(30) Foreign Application Priority Data

Mar. 3, 2003 (GB) .................................. 0304823.8

(51) Int. Cl.
*A61M 5/00* (2006.01)
*A61M 5/178* (2006.01)
(Continued)

(52) U.S. Cl.
CPC ...... *A61M 5/31528* (2013.01); *A61M 5/3155* (2013.01); *A61M 5/31533* (2013.01);
(Continued)

(58) Field of Classification Search
CPC .......... A61M 5/31541; A61M 5/31593; A61M 2205/581; A61M 5/31501;
(Continued)

(56) References Cited

U.S. PATENT DOCUMENTS

| 533,575 A | 2/1895 | Wilkens |
|---|---|---|
| 4,865,591 A | 9/1989 | Sams |

(Continued)

FOREIGN PATENT DOCUMENTS

| CA | 2138528 C | 12/1998 |
|---|---|---|
| CA | 2359375 A1 | 7/2000 |

(Continued)

OTHER PUBLICATIONS

"Pen-injectors for medical use—Part 1: Pen-injectors—Requirements and test methods," International Standard, reference No. ISO 11608-1:2000(E), first edition Dec. 15, 2000, 32 pages.

*Primary Examiner* — Rebecca E Eisenberg
(74) *Attorney, Agent, or Firm* — Fish & Richardson P.C.

(57) ABSTRACT

The present disclosure is directed to a dose setting mechanism that may be used with a drug delivery device. The dose setting mechanism may include an inner body having a helical thread along an outer cylindrical surface of the inner body, and a drive sleeve for driving a piston rod in an axial direction, the drive sleeve positioned within at least a portion of the inner body. The dose setting mechanism may further include a dose dial sleeve rotatably engaged with the helical thread of the inner body and a dial grip connected to the dose dial sleeve and releasably connected to the drive sleeve. Further when a dose is set, the dial grip is rotated so that both the dose dial sleeve and the drive sleeve rotate with respect to the inner body.

10 Claims, 7 Drawing Sheets

Related U.S. Application Data continuation of application No. 13/667,449, filed on Nov. 2, 2012, now Pat. No. 8,873,782, which is a continuation of application No. 13/280,903, filed on Oct. 25, 2011, now Pat. No. 8,574,198, which is a continuation of application No. 12/453,626, filed on May 15, 2009, now Pat. No. 8,070,727, which is a continuation of application No. 10/790,024, filed on Mar. 2, 2004, now Pat. No. 7,553,299.

(51) Int. Cl.
*A61M 5/315* (2006.01)
*A61M 5/24* (2006.01)

(52) U.S. Cl.
CPC .......... *A61M 5/31551* (2013.01); *A61M 5/24* (2013.01); *A61M 5/2422* (2013.01); *A61M 5/3156* (2013.01); *A61M 5/31501* (2013.01); *A61M 5/31511* (2013.01); *A61M 5/31526* (2013.01); *A61M 5/31541* (2013.01); *A61M 5/31583* (2013.01); *A61M 5/31585* (2013.01); *A61M 5/31593* (2013.01); *A61M 2205/581* (2013.01); *A61M 2205/582* (2013.01)

(58) Field of Classification Search
CPC .......... A61M 5/31511; A61M 5/31526; A61M 5/31533; A61M 5/3155; A61M 5/31585
See application file for complete search history.

(56) References Cited

U.S. PATENT DOCUMENTS

| | | |
|---|---|---|
| 5,092,842 A | 3/1992 | Bechtold et al. |
| 5,226,895 A | 7/1993 | Harris |
| 5,226,896 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,378,233 A | 1/1995 | Haber et al. |
| 5,383,865 A | 1/1995 | Michel |
| 5,391,157 A | 2/1995 | Harris et al. |
| 5,480,387 A | 1/1996 | Gabriel et al. |
| 5,505,704 A | 4/1996 | Pawelka et al. |
| 5,582,598 A | 12/1996 | Chanoch |
| 5,584,815 A | 12/1996 | Pawelka et al. |
| 5,626,566 A | 5/1997 | Petersen et al. |
| 5,674,204 A | 10/1997 | Chanoch |
| 5,679,111 A | 10/1997 | Hjertman et al. |
| 5,688,251 A | 11/1997 | Chanoch |
| 5,807,346 A | 9/1998 | Frezza |
| 5,820,602 A | 10/1998 | Kovelman et al. |
| 5,851,079 A | 12/1998 | Horstman et al. |
| 5,921,966 A | 7/1999 | Bendek et al. |
| 5,957,896 A | 9/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,562,006 B1 | 5/2003 | Hjertman et al. |
| 6,613,023 B2 | 9/2003 | Kirchhofer et al. |
| 6,699,224 B2 | 3/2004 | Kirchhofer et al. |
| 6,899,698 B2 | 5/2005 | Sams |
| 6,932,794 B2 | 8/2005 | Giambattista et al. |
| 6,936,032 B1 | 8/2005 | Bush, Jr. et al. |
| 7,169,132 B2 | 1/2007 | Bendek et al. |
| 7,241,278 B2 | 7/2007 | Moller |
| 7,678,084 B2 | 3/2010 | Judson et al. |
| 7,850,662 B2 | 12/2010 | Veasey et al. |
| 8,187,233 B2 | 5/2012 | Harms et al. |
| 2002/0052578 A1 | 5/2002 | Moller |
| 2002/0120235 A1 | 8/2002 | Enggaard |
| 2002/0165499 A1 | 11/2002 | Slate et al. |
| 2003/0050609 A1 | 3/2003 | Sams |
| 2004/0059299 A1 | 3/2004 | Moller |
| 2004/0097883 A1 | 5/2004 | Roe |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2007/0016143 A1 | 1/2007 | Miller et al. |
| 2009/0275916 A1 | 11/2009 | Harms et al. |

FOREIGN PATENT DOCUMENTS

| | | |
|---|---|---|
| EP | 0496141 A1 | 7/1992 |
| EP | 0897729 A2 | 2/1999 |
| EP | 0937471 | 8/1999 |
| EP | 0937476 A2 | 8/1999 |
| EP | 0937477 | 8/1999 |
| EP | 1776975 A2 | 4/2007 |
| WO | WO 91/14457 | 10/1991 |
| WO | 93/07922 A1 | 4/1993 |
| WO | 93/24160 A1 | 12/1993 |
| WO | WO 96/25965 | 8/1996 |
| WO | 99/38554 A1 | 8/1999 |
| WO | 01/10484 | 2/2001 |
| WO | 02/30495 A2 | 4/2002 |
| WO | WO 02/053214 | 7/2002 |
| WO | 02/092153 A2 | 11/2002 |
| WO | 03/080160 A1 | 10/2003 |
| WO | 2006/084876 A1 | 8/2006 |

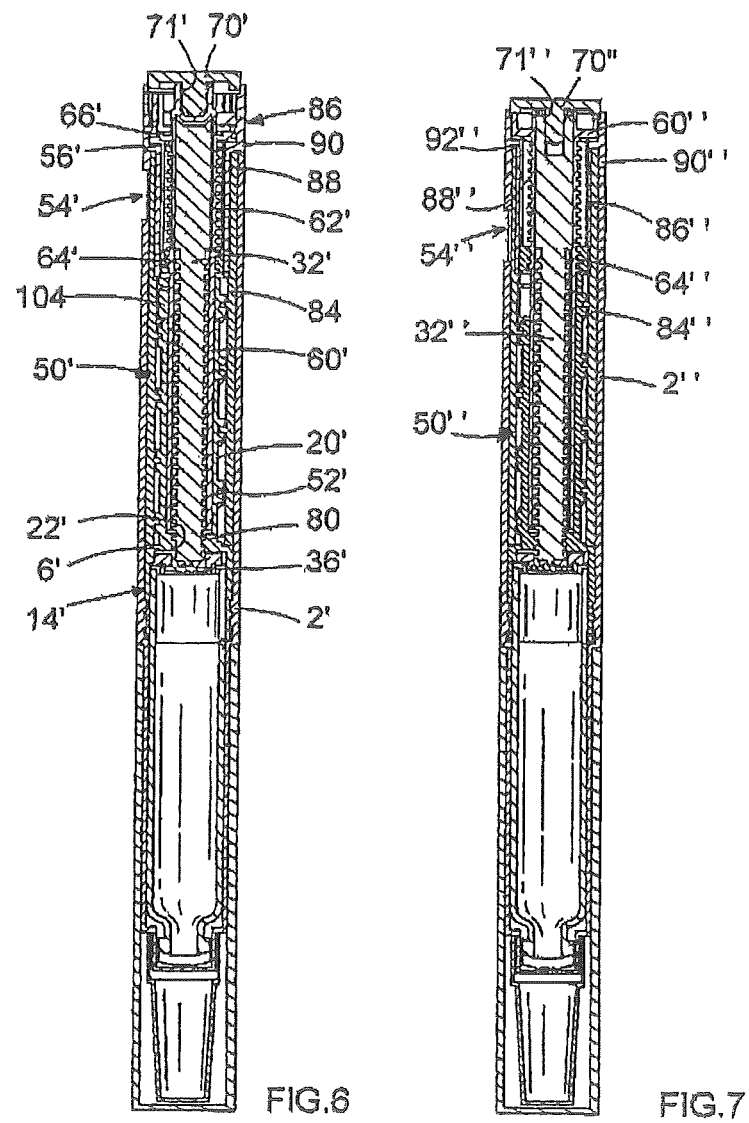

DRIVE MECHANISMS SUITABLE FOR USE IN DRUG DELIVERY DEVICES

THE TECHNICAL FIELD OF THE INVENTION

The present invention relates to drive mechanisms suitable for use in drug delivery devices, in particular pen-type injectors, having dosage setting means, enabling the administration of medicinal products from a multi-dose cartridge. In particular, the present invention relates to such drug delivery devices where a user may set the dose.

DESCRIPTION OF RELATED ART

Such drug delivery devices have application where regular injection by persons without formal medical training occurs, i.e., patients. This is increasingly common amongst those having diabetes where self-treatment enables such persons to conduct effective management of their diabetes.

These circumstances set a number of requirements for drug delivery devices of this kind. The device must be robust in construction, yet easy to use in terms of the manipulation of the parts, understanding by a user of its operation and the delivery of the required dose of medicament. Dose setting must be easy and unambiguous. In the case of those with diabetes, many users will be physically infirm and may also have Impaired vision requiring the drive mechanism to have low dispensing force and an easy to read dose setting display. Where the device is to be disposable rather than reusable, the device should be cheap to manufacture and easy to dispose of (preferably being suitable, for recycling). To meet these requirements the number of parts required to assemble the device and the number of material types the device is made from need to be kept to a minimum.

User operated drug delivery devices are well known within the medical field.

WO9938554A2 teaches an injection syringe for apportioning set doses of a medicine from a cartridge wherein a drive mechanism comprising a unidirectional coupling (i.e., a ratchet) is disclosed which allows correction of a set overdose without dispensing the set amount of fluid or requiring the dismantling of the cartridge.

EP0937471A2 discloses a medication delivery pen having a drive mechanism comprising a unidirectional coupling (i.e, a ratchet) located between the rod barrel tube and the housing. The disclosed drive mechanism is of the direct type, which means that relatively high actuation force is required by the user.

Surprisingly it was found that a drive mechanism comprising a unidirectional coupling and a clutch mechanism according to instant invention provides lower actuation forces for the user or, alternatively, allows application of greater volumes of medicinal products. Additionally the drive mechanism of instant invention provides the advantage of intuitive, safe, and easy to use correction of a set dose and it further provides improved protection of the working parts from dust and debris.

DESCRIPTION OF THE INVENTION

Therefore, a first object of instant invention is a drive mechanism for use in a drug delivery device comprising:

a housing having an internal and an external thread;

a piston rod having a non-circular cross section, and which is threadedly engaged with the internal thread of the housing;

a unidirectional coupling located between the housing and the piston rod;

a dose dial sleeve, which is threadedly engaged with the external thread of the housing and being rotatable with respect to the housing;

a drive sleeve, located between the housing and the piston rod, which Is axially displaceable but not rotatable with respect to the piston rod; and a clutch means located between the drive sleeve and the dose dial sleeve, which a. when the dose dial sleeve and the drive sleeve are de-coupled by the said clutch means, rotation of said dose dial sleeve with respect to said drive sleeve is allowed; and b. when the dose dial sleeve and drive sleeve are coupled by the said clutch means rotation of the does dial sleeve with respect to the said drive sleeve is prevented.

The term "drug delivery device" according to instant invention shall mean a single-dose or multi-dose, disposable or re-useable device designed to dispense a selected dose of a medicinal product, preferably multiple selected doses, e.g. insulin, growth hormones, low molecular weight heparins, and their analogues and/or derivatives etc. Said device may be of any shape, e.g. compact or pen-type. Dose delivery may be provided through a mechanical (optionally manual) or electrical drive mechanism or stored energy drive mechanism, such as a spring, etc. Dose selection may be provided through a manual mechanism or electronic mechanism. Additionally, said device may contain components designed to monitor physiological properties such as blood glucose levels, etc. Furthermore, the said device may comprise a needle or may be needle-free. In particular, preferred embodiment the term drug delivery device shall mean a disposable multi-dose pen-type device having mechanical and manual dose delivery and dose selection mechanisms, which is designed for regular use by persons without formal medical training such as patients. Preferably, the drug delivery device is of the Injector-type. Optionally, the drug delivery device according to instant invention further comprises a nut threadedly connected to the drive sleeve and rotatable with respect to the drive sleeve and which is engaged with the dose dial sleeve to allow axial displacement of the nut with respect to the dose sleeve, but not rotation of the nut with respect to the dose dial sleeve.

The term "housing" according to instant invention shall preferably mean an exterior housing ("main housing", "body, "shell") or interior housing ("inner body", "Insert") having an internal and an external thread. The housing may be designed to enable the safe, correct, and comfortable handling of the drug delivery device or any of its mechanisms. Usually, it is designed to house, fix, protect, guide, and/or engage with any of the inner components of the drug delivery device (e.g., the drive mechanism, cartridge, plunger, piston rod) by limiting the exposure to contaminants, such as liquid, dust, dirt etc. In general, the housing may be unitary or a multipart component of tubular or non-tubular shape. Usually, the exterior housing serves to house a cartridge from which a number of doses of a medicinal product may by dispensed.

In a more specific embodiment of instant invention, the interior housing is provided with a plurality of maximum dose stops adapted to be abutted by a radial stop provided on the dose dial sleeve.

In a more particular embodiment of instant invention, the interior housing comprises a web having an opening through which the piston may extend. A first cylindrical portion may extend from from the first end of the web, and a second and a third cylindrical portion may extend from the second end of the web. Preferably, the second cylindrical portion is provided with an internal thread.

In a further embodiment of Instant invention, the insert comprises a web having an opening through which the piston may extend. A first cylindrical portion may extend from a first end of the web, a boss provided on a second end of the web and a cylindrical portion extending away from the web about a periphery of the boss. Optionally, the boss is provided with an internal thread or a radial flange being spaced from the web with a cylindrical portion extending away from the web about a periphery of the radial flange The term "engaged" according to instant invention shall particularly mean the interlocking of two or more components of the drive mechanism/drug delivery device, e.g. a spline or thread connection, preferably the interlocking of helical threads of components ("threadedly enaged").

The term "thread" according to instant invention shall preferably mean a full or part thread, e.g., a cylindrical spiral rib/groove, usually of helical nature, located on the internal and/or external surface of a component of the drug delivery device ("internal thread" and/or "external thread"), having an essentially triangular or square or rounded section designed to allow continuous free rotational and/or axial movement between components. Optionally, a thread may be further designed to prevent rotational or axial movement of certain components in one direction.

The term "dose dial sleeve" according to instant invention shall mean an essentially tubular component of essentially circular cross-section having either:

a. a) both an Internal and external thread, or
b. b) an internal thread, or
c. c) an external thread, said dose dial sleeve may be made or constructed of one or more parts. Preferably, the "dose dial sleeve" according to instant invention comprises an internal helical thread, which is threadedly engaged with the external thread of the housing, particularly the insert.

In yet another preferred embodiment the dose dial sleeve is designed to indicate a selected dose of a dispensable product. In still another preferred embodiment of instant invention, the maximum selectable dose may be determined by the abutment of a radially directed lug on the dose dial sleeve with a catch means on the insert following the maximum angular displacement of the dose dial sleeve with respect to the housing. Preferably, the radially directed lug extends parallel to a longitudinal axis of the dose dial sleeve.

Generally, the term "catch means" according to instant Invention shall mean any constructive feature, which serves as a counterpart to the lug on the dose dial sleeve and which is preferably located on the outer surface of the insert, and which together with the lug of the dose dial sleeve defines the maximum allowable dosage of the mechanism. Optionally, the catch means may be a groove extending about a central land, e.g., a central land being wedge shaped such that a first edge extends radially less far than a second opposite edge to define a sloping surface between the first edge and the second edge.

Indication of the selected dose on the dose dial sleeve may be achieved by use of markings, symbols, numerals, etc., e.g., printed on the external surface of the dose dial sleeve or an odometer, or the like.

In a more specific embodiment of instant invention, the dose dial sleeve comprises a first section of a first diameter and a second section of second diameter.

The term "lead" according to instant invention shall preferably mean the axial distance a nut would advance in one complete revolution; preferably "lead" shall mean the axial distance through which a component having a helical thread, i.e., dose dial sleeve, piston rod, etc., of the drive mechanism travels during one rotation. Therefore lead is a function of the pitch of the thread of the relevant component.

The term "pitch" according to instant invention shall preferably mean the distance between consecutive contours of the helical thread, measured parallel to the axis of the helical thread.

The term "drive sleeve" according to Instant invention shall mean any essentially tubular component of essentially circular cross-section and which is further located between the housing, preferably the internal housing and the piston rod, and which is axially displaceable but not rotatable with respect to the piston rod. The drive sleeve of the invention is further releasably connected to the dose dial sleeve by a clutch means and is further engaged with the piston rod at the distal and/or proximal end. The drive sleeve may further comprise a first section of the first diameter located between the insert and the piston rod and a second section of second diameter located between the piston rod and the dose dial sleeve.

The term "releasibly connected" according to instant invention shall preferably mean that two components of instant mechanism or device are reversibly joined to each other, which allows coupling and decoupling, e.g., by means of a clutch.

The term "piston rod" according to instant invention shall mean a component adapted to operate through/within the housing, designed to translate axial movement through/within the drug delivery device, preferably from the drive sleeve to the piston, for the purpose of discharging/dispensing an injectable product. Said piston rod may be flexible or not. It may be a simple rod, a lead-screw, or the like. The "piston rod" according to instant invention shall further mean a component having a non-circular cross-section and an external thread located on its first end. It may be made of any suitable material known by a person skilled in the art.

The term "first end" according to instant invention shall mean the proximal end. The proximal end of the device or a component of the device shall mean the end, which is closest to the dispensing end of the device.

The term "second end" according to instant invention shall mean the distal end. The distal end of the device or a component of the device shall mean the end, which is furthest away from the dispensing end of the device.

The term "clutch means" according to instant invention shall mean any means, which releasibly connects the dose dial sleeve and the drive sleeve and which is located between the drive sleeve and the dose dial sleeve, and which allows rotation of the dose dial sleeve with respect to said drive sleeve when the dose dial sleeve and the drive sleeve are de-coupled, and which prevents rotation of the dose dial sleeve with respect to the drive sleeve when the dose dial sleeve and drive sleeve are coupled. According to instant Invention the term "clutch means" encompasses any clutch mechanism engaging for the purpose of reversibly locking two components in rotation, e.g., by use of axial forces to engage a set of face teeth (saw teeth, dog teeth, crown teeth) or any other suitable frictional faces.

In still another embodiment of instant invention, the drive mechanism further comprises a clicker means. Preferably, the "clicker means" shall mean any means located between the dose dial sleeve and the drive sleeve, which upon relative rotation of the said drive sleeve and the said dose dial sleeve causes a series of audible and/or tactile clicks.

Such a clicker means may comprise a plurality of longitudinally extending teeth and a flexible toothed member, one of the plurality of teeth and the toothed member being provided on the dose dial sleeve, the other being provided on the drive sleeve.

The term "unidirectional coupling" according to instant invention shall mean any mechanism located between the housing and the piston rod, which allows movement of the piston rod in the proximal direction and prevents movement of the piston rod in the distal direction, preferably acting between the non-circular cross section of the piston rod and the housing.

A second aspect of Instant invention provides an assembly for use in a drug delivery device comprising the drive mechanism according to instant invention.

A third aspect of the present invention provides a drug delivery device comprising the drive mechanism or the assembly according to instant invention.

A fourth aspect of the present invention provides a method of assembling a drug delivery device comprising the step of providing a drive mechanism or an assembly according to instant invention.

A fifth aspect of instant invention is the use of a drug delivery device according to instant Invention for dispensing a medicinal product, preferably dispensing a pharmaceutical formulation (e.g. solution, suspension etc.) comprising an active compound selected from the group consisting of insulin, growth hormone, low molecular weight heparin, their analogues and their derivatives.

BRIEF DESCRIPTION OF THE DRAWINGS

Without any limitation, the instant invention will be explained in greater detail below in connection with a preferred embodiment and with reference to the drawings in which:

FIG. 6 allows a sectional view of a second embodiment of the drug delivery device in accordance with the prevent invention;

FIG. 7 shows a sectional side view of a third embodiment of the drug delivery device in accordance with the present invention;

DETAILED DESCRIPTION OF THE EMBODIMENTS

Example 1

Figure 1:
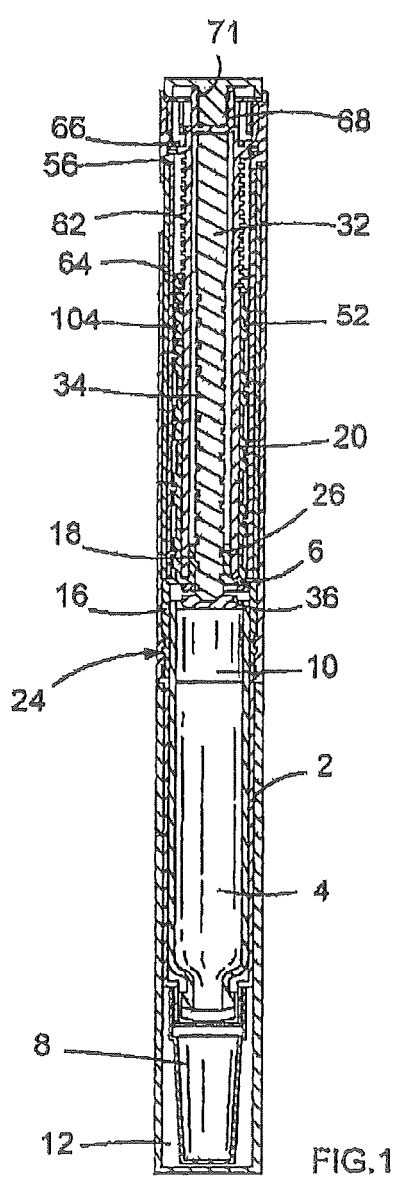
FIG. 1 shows a sectional view of a first embodiment of the drug delivery device, in accordance with the present invention in a first, cartridge full, position.
Figure 2:
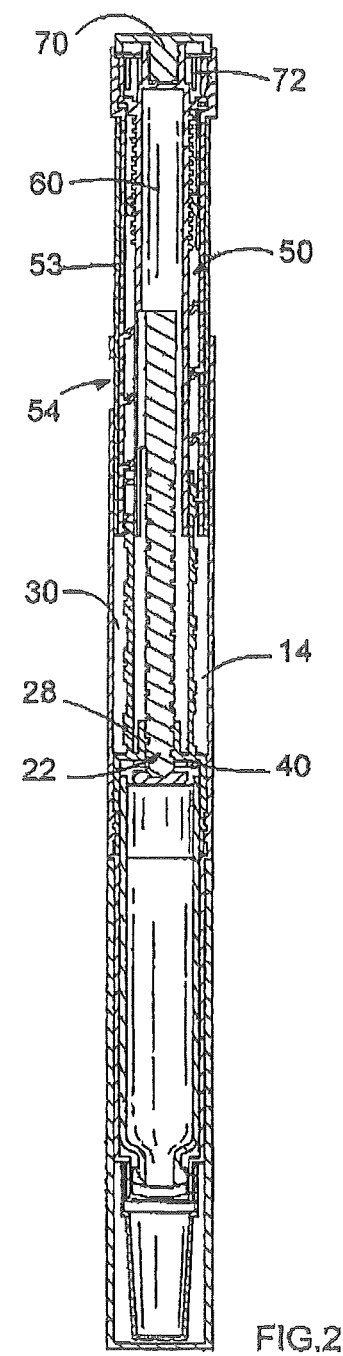
FIG. 2 shows a sectional view of the drug delivery device of FIG. 1 in a second, maximum first dose dialed, position.

Referring to FIGS. 1 to 5 there is seen a drug delivery device in accordance with the first embodiment of the present invention. The device comprises a housing 2 within which are located a cartridge 4 containing medicinal product, means for setting or selecting the dose of medicinal product to be expelled and means for expelling the selected dose of medicinal product. The housing 2 is generally cylindrical in shape and is divided into two compartments by a web 6 to be described in more detail below. The cartridge 4 is located within a first part of the housing 2. The dose setting means and the means for expelling the selected dose of medicinal product are retained; that is held, within a second part of the housing 2. An advantage of a one piece housing enclosing the cartridge 4 together with the dose setting and dose expelling means lies in the ease of assembly of the product. This is in part due to the reduced number of components in the pen-type injector. Also, the unitary nature of the housing 2 means that the pen-type injector is mode robust.

The cartridge 4 may be secured in position in the first part of the housing 2 by any suitable means. A needle unit may be secured to a first end of the cartridge 4. A temporary covering 8 is shown in this position in the Figures. The cartridge 4 further comprises a displaceable piston 10. Advancing the piston 10 towards the first end of the cartridge 4 causes the medicinal product to be expelled from the cartridge 4 through the needle unit. A cap 12 Is provided to cover the needle unit when the injector is not in use. The cap 12 may be releasably secured to the housing 2 by any suitable means.

The dose setting means and the mean for expelling the selected dose of medicinal product will now be described in more detail. The web 6 dividing the housing 2 is a part of an insert 14 located within the housing 2. The insert 14 comprises a first cylindrical portion 16 extending from a first side of the web 6 and second and third cylindrical portions 18,20 extending from a second side of the web 6. The web 6 is provided with a circular opening 22 extending through the web 6.

The first cylindrical portion 16 extends from a periphery of the web 6. The insert 14 is secured to the housing 2 by way of the first cylindrical portion 16 by any suitable means. In the illustrated embodiment features 24 are provided within the housing 2 and on an outer surface of the first cylindrical portion 16 to enable the insert to be a snap fit to the housing 2.

The second cylindrical portion 18 extends a small distance from the second aide of the web 6 about a periphery of the opening 22. An Internal surface of the second cylindrical portion Is provided With a thread 26.

The third cylindrical portion 20 extends substantially within the housing 2 from the second side of the web 6. The diameter of the third cylindrical portion 20 is such that a first channel 28 is formed between an outer surface of the second cylindrical portion 20 and an inner surface of the third cylindrical portion. A second channel 30 is formed between an outer surface of the third cylindrical portion 20 and the housing 2.

A piston rod 32 extends through the opening in the web 6. The piston rod 32 is generally elongate and is provided with a thread 34 extending from a first end of the piston rod 32. The thread 34 of the piston rod 32 engages the thread of the inner surface of the second cylindrical portion 18 of the insert 14. The first end of the piston rod 32 Is provided with a pressure foot 36. In use the pressure foot 36 is disposed on the first side of the web 6 to about the cartridge piston 10.

Ratchet means 40 are located adjacentthe web 6 on the first side of the web 6. The ratchet means 40 serve the purpose of allowing the piston rod 32 only to rotate through the insert 14 in a single direction. Due to the one piece construction of the housing, the ratchet means can be made larger than in known devices and so Is stronger (more rigid).

A dose dial sleeve 50 of generally cylindrical form comprises a first section of first diameter and a second section of second diameter. The first section Is located within the second channel 30. An inner surface of the first section and the outer surface of the third cylindrical portion 20 are provided with interengaging features to provide a helical thread 52 between the insert 14 and the dose dial sleeve 50. In the illustrated embodiment this was achieved by a helical track provided on the outer surface of the third cylindrical portion 20 within which a helical rib provided on the inner surface of the dose dial sleeve 50 may run. This enables the dose dial sleeve 50 to rotate about and along the third cylindrical portion 20 of the insert 14.

An outer surface of the first section of the dose dial sleeve 50 is provided with graphics 53. The graphics are typically a sequence of reference numerals. The housing 2 Is provided with an aperture or window 54 through which a portion of the graphics, representing a dosage value selected by the user, may be viewed.

The graphics 53 may be applied to the dose dial sleeve 50 by any suitable means. In the illustrated embodiment, the graphics 53 are provided In the form of a printed label encircling the dose dial sleeve 50. Alternatively the graphics may take the form of a marked sleeve clipped to the dose dial sleeve 50. The graphics may be marked in any suitable manner, for example by laser marking.

It is an advantage of this arrangement that the helical thread 52 is formed within the dose dial sleeve between the dose dial sleeve and the insert. As can be seen this means there is no direct route from outside the injector to the working surfaces of the helical thread. Should dust or dirt enter the pen this will tend to occur between the housing and the dose dial sleeve where there are no working parts with which to interfere. This is not the case for known devices In which a helical thread Is formed between the housing and an interior moving surface. In addition because of the narrower diameter of the helical thread 52 formed between the dose dial sleeve and the drive sleeve in comparison to a similar thread formed between the housing and the dose dial sleeve, the helical thread 52 Is more efficient and easier to overhaul. This arrangement also produces an improvement in the dose size that can be delivered for a particular linear travel of the dose expelling means.

The second section of the dose dial sleeve 50 is preferably of the same outer diameter as the housing 2. Within the dose dial sleeve 50 there is a shoulder 56 between the first section of the dose dial sleeve 50 and the second section of the dose dial sleeve 50.

A drive sleeve 60 of generally cylindrical form comprises a first part of first diameter and a second part of second diameter. A first end of the first part is located within the first channel 28 of the insert 14 in the position shown in FIG. 1. The first part of the drive sleeve 60 may be considered as comprising a first portion aligned with a second portion. More generally in the position shown In FIG. 1 the first portion of the drive sleeve 60 is located between the insert 14 and the piston rod 32 while the second portion is located between the piston rod 32 and the dose dial sleeve 50.

A second end of the piston rod 32 end en intimal surface of the drive sleeve 60 are splined together such that no relative rotation may occur between these parts, only longitudinal displacement.

The outer surface of the second portion of the first part of the drive sleeve 60 is provided with a helical thread 62. A nut 64 Is provided on the helical thread 62 between the drive sleeve 60 and the dose dial sleeve 50. The dose dial sleeve 50 and the nut 64 arc splined together by spline means to prevent relative rotation between the nut 64 and the dose dial sleeve 50.

The second part of the drive sleeve 60 is of larger diameter then the first part of the drive sleeve 60. There is a step 66 between the first part of the drive sleeve 60 and the second part. The second part of the drive sleeve 60 is seated within the second section of the dose dal sleeve 50. The shoulder 56 of the dose dial sleeve 50 and the step 66 of the drive sleeve 60 are adapted to be releasably engagable with one another to form a clutch means. When, as in FIG. 1, the dose dial sleeve 50 and the drive sleeve 60 are not in engagement the dose dial sleeve 50 is able to rotate with respect to the drive sleeve 60. Conveniently, the clutch means comprises a plurality of radially extending longitudinally directed teeth provided respectively on the shoulder 56 of the dose dial sleeve 50 and the step 66 of the drive sleeve 60. When the dose dial sleeve 50 and the drive sleeve 60 are not forced together the respective teeth will ride over one another. Preferably, the radial separation of the respective teeth corresponds to a unit dosage.

The second part of the drive sleeve 60 further comprises a central receiving area 68 having a peripheral recess. A button 70 of generally "T" shaped configuration is provided, the stem of which is retained within the receiving area. The stem of the button 70 Is provided with a peripheral bead 71 that Is retained in the peripheral recess, the button 70 being able freely to rotate with respect to the. drive sleeve 60, but being retained axially therewith.

Clicker moans are provided between the second section of the dose dial sleeve 50 and the second part of the drive sleeve 60. In the illustrated embodiment, the internal surface of the second section of the dose dial 50 is provided with a plurality of longitudinally extending teeth. The radial separation of the teeth preferably corresponds to a unit dosage. The second part of the drive sleeve 60 carries a flexible toothed member 72. Relative rotation between the dose dial sleeve 50 and the drive sleeve 60 will cause the flexible toothed member 72 to ride over the teeth to produce a series of clicks.

In FIG. 1, the injector is provided with!a filled cartridge 4. To operate the Injector a user must first select a dose. To set a dose the dose dial sleeve 50 is rotated by manipulating the second section of the dose dial sleeve 50 with respect to the housing 2 until the desired dose value is visible through the window 54. This action draws the dose dial 50 along the second cylindrical portion of the insert 14. The drive sleeve 60 cannot rotate since it is splined to the piston rod 32. The piston rod 32 does not rotate due to the action of the ratchet means 40. The drive sleeve 60 is carried away from the web 6 along the piston rod 32 by the dose dial sleeve 50 as the dose dial sleeve 50 moves out from the housing 2. The relative rotation between the dose dial sleeve 50 and the drive sleeve 60 causes the flexible toothed member 72 to ride over the ridges in the drive sleeve 60 to create a series of clicks. This Is an audible confirmation of the dose being dialed.

Since the nut 64 is splined to the dose dial sleeve 50, the relative rotation between the dose dial sleeve 50 and the drive sleeve 60 causes the nut 64 to precess along the helical thread 62 of the drive sleeve 60.

Figure 3:
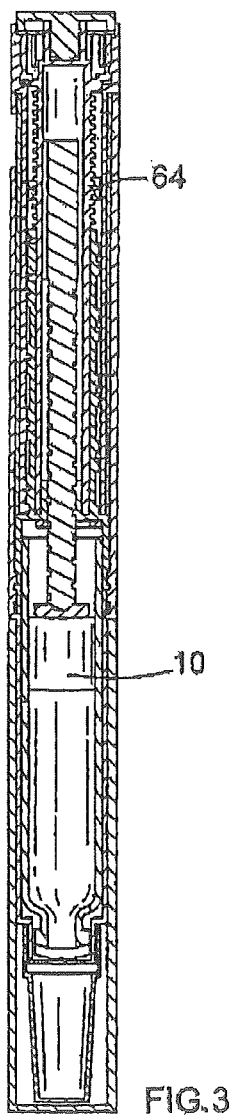
FIG. 3 shows a sectional view of the drug delivery device of FIG. 1 in a third, maximum first dose dispensed, position.

Once a desired dose has been set (as shown for example in FIG. 2), to deliver the dose the user depresses the button 70 to urge the button 70 towards the first end of the housing 2. When the button 70 is depressed the second part of the drive sleeve 60 is driven into the second section of the dose dial sleeve 50 to engage the clutch means therebetween to prevent relative rotation between the dose dial sleeve 60 and the drive sleeve 60. The drive sleeve 60 may still rotate with respect to the button 70. Further longitudinal movement of the button 70 causes the dose dial sleeve 50 (together with the drive sleeve 60) to rotate towards the fire end of the injector. Since the piston rod 32 is splined to the drive sleeve 60, the piston rod 32 is also rotated through the insert 14 and the ratchet means 40 towards the first end of the injector, thereby to advance the cartridge piston 10 and expel the desired dose of medicinal product. The piston rod 32 continues to advance until the drive sleeve 60 and dose dial sleeve 50 have returned to their Initial positions (FIG. 3).

It can be seen that the dose selecting means and the dose expelling means extend beyond a second end of the housing 2 as the dose is selected and are returned within the housing 2 as the selected dose is expelled.

Figure 4:
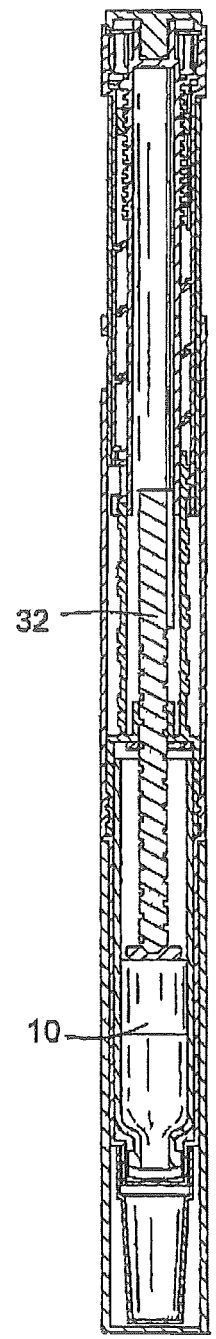
FIG. 4 shows a sectional view of the drug delivery device of FIG. 1 in a fourth, final dose dialed, position.
Figure 5:
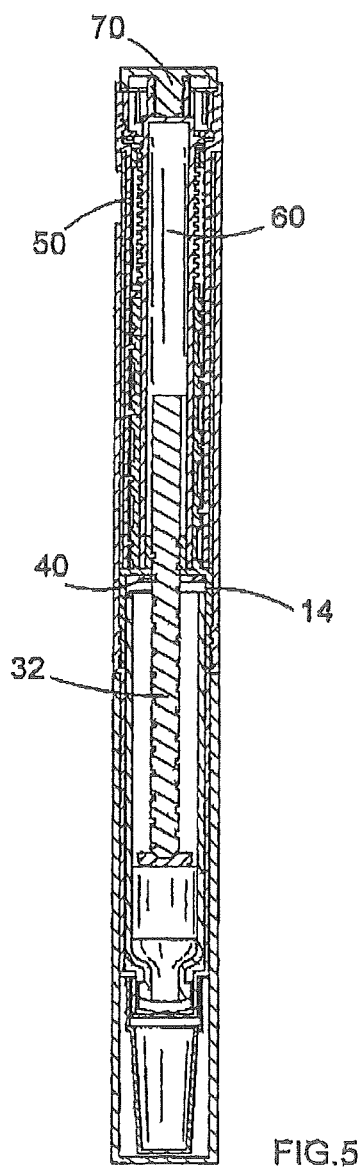
FIG. 5 shows a sectional view of the drug delivery device of FIG. 1 in a fifth, final dose dispensed, position.

Further dosages may be delivered as required. FIG. 4 shows en example of a subsequently selected dosage. It will be noted that the nut 64 has advanced further along the helical thread 62 of the drive sleeve 60. The position of the nut 64 along the helical thread 62 corresponds to the amount of medicinal product remaining in the cartridge 4, such that when the nut 64 reaches the end of the helical thread 62 (in the illustrated embodiment adjacent to the step 66 of the drive sleeve 60) and can rotate no further this corresponds to no medicinal product remaining in the cartridge 4. It will be seen that if a user seeks to select a quantity of medical product greater than that remaining in the, cartridge 4, this cannot be done since when the nut 64 stops rotating the dose dial sleeve 50 and the drive sleeve 60 will become locked together preventing rotation of the dose dial sleeve 50 and setting of a larger dose. FIG. 5 shows an injector according to the present invention in which the entire medical product within the cartridge 4 has been expelled.

A second embodiment of the present invention is disclosed in FIG. 6. Like reference numerals are used to refer to like parts as between the first and second embodiments.

The piston rod 32' shown in FIG. 6 has e dual start thread. The piston foot 36' is reversible. This has advantages in manufacture. As can be seen the structure of the insert 14' has been revised. The first side of the web 6' is substantially unchanged. The other side of the web is now provided with a boss 80. A cylindrical portion 20' extends away from the web 6' about a periphery of the boss 80. Threaded opening 22' extends through the web 6' and the boss 80. An end of the cylindrical portion 20' of the insert 14' remote from the web 6' is provided with a stop in the form of a land 104.

The dose dial sleeve 50' is of modified construction. The dose dial sleeve comprises a first cylindrical portion 84 rigidly connected to a second generally cylindrical portion 86. An Inner surface of the first cylindrical portion 84 and the outer surface of the cylindrical portion 20' of the insert 14' are provided with interengaging features to provide a helical thread 52' between the insert 14' and the dose dial sleeve 50'. An outer surface of the first cylindrical portion 84 is provided with the dose graphics. The housing 2' is provided with an aperture or window 54' through which a portion of the graphics may be viewed.

The second generally cylindrical portion 88 comprises a first cylindrical section 88 and a second cylindrical section 90. The first section 88 is rigidly keyed to an inner surface of the first portion 84 of the dose dial sleeve 50'. The second section 90 Is preferably of the same outer diameter as the housing 2'. Within the dose dial sleeve 50' there is a shoulder 50' between the first section 86 and the second section 90.

A nut 64' is provided on the helical thread 62' between the drive sleeve 60' end the first cylindrical section 86 of the dose dial sleeve 50'. The first cylindrical section 88 and the nut 64' are splined together by spline means to prevent relative rotation between the nut 64' and the dose dial sleeve 50'.

The shoulder 56' of the dose dial sleeve 50' and a step 66' of a drive sleeve 60' are adapted to be releasably engagable with on another to term a clutch means. When, as In FIG. 6, the dose dial sleeve 50' and the drive sleeve 60' are not in engagement the dose dial sleeve 50' is able to rotate with respect to the drive sleeve 60'. Conveniently, the clutch moans comprises a plurality of radially extending longitudinally directed teeth provided respectively on the shoulder 56' of the dose dial sleeve 50' and the stop 88' of the drive sleeve 60'. When the dose dial sleeve 50' and the drive sleeve 80' are not forced together the respective teeth will ride over one another.

It will be seen that the structure of the drive sleeve 60' has also been modified. The second end of the piston rod 32' is provided with a scooped surface within which a domed part 90 of the drive sleeve 60' may extend. The domed part 90 is centrally located within a second part of the drive sleeve 60' at a first end of the receiving area.

The button 70' is of generally "T" shaped configuration. The stem of the button 70' is retained within the receiving area. The stem of the button 70' is provided with a peripheral bead 71' that is retained in the peripheral recess, the button 70' being able freely to rotate with respect to the drive sleeve 60', but being retained axially therewith.

When the button 70' is depressed the drive sleeve 60' is urged into contact with the dose dial sleeve 50' such that the clutch means are engaged. At the same time, the scooped surface of the piston rod 32' and the domed surface of the drive sleeve approach but do not contact one another. The advantage of this structure is that it enables the overall length of the device to be reduced thereby enabling easier operation of the device when expressing fluid from a cartridge.

A further embodiment of the button 70" and the dose dial sleeve 50" can be seen in FIG. 7. Again like reference numerals are used to refer to like parts. In the embodiment of FIG. 7, the overall length of the device may be reduced still further. The second end of the piston rod 32" Is generally U-shaped. The limbs of the U-shape are received within a second part of the drive sleeve 60". A central receiving area of the drive sleeve 60" is defined by limbs (not shown) located in use between the limbs formed on the second end of the piston rod 32". The button 70" is of generally "T" shaped configuration. The stem of the button 70" is retained within the receiving area. The stem of the button 70" Is provided with a peripheral bead 71" that is retained in the peripheral recess, the button 70" being able freely to rotate with respect to the drive sleeve 60", but being retained axially therewith.

The second generally cylindrically portion 80" of the dose dial sleeve 50" comprises a first cylindrical section 88" and a second cylindrical section 90" connected by a radial flange 92 extending from a part of the second section, the first section 88" being rigidly keyed to an inner surface of the first portion 84" of the dose dial sleeve 50", and the second section 90" being of the same outer diameter as the housing 2".

Figure 8:
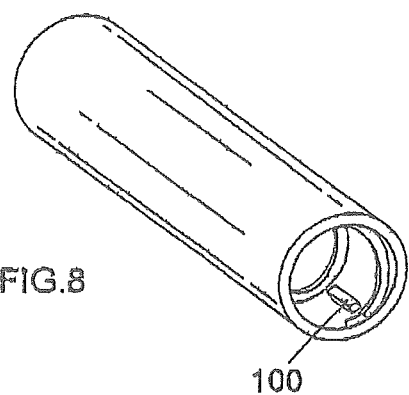
FIG. 8 shows a perspective view of a dose dial sleeve for use in conjunction with the present invention.
Figure 9:
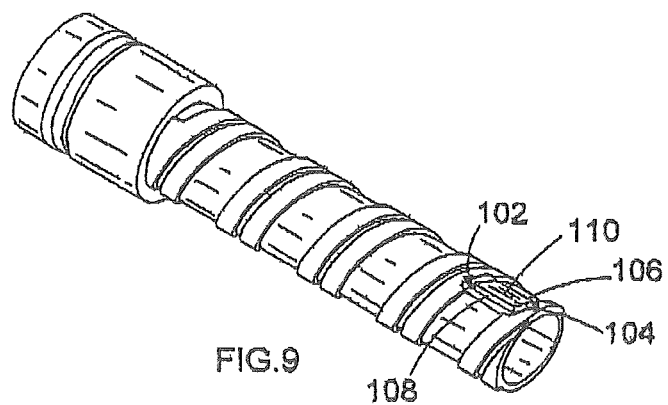
FIG. 9 shows a perspective view of an insert for use with the dose dial sleeve of FIG. 8.

In each of FIGS. 6 and 7, there is a further modification to each of the dose dial sleeve and the insert. This may be seen more clearly with reference to FIGS. 8 and 9.

At a first end of the dose dial sleeve there is located on an internal surface a radially directed lug 100 extending generally parallel to a longitudinal axis of the sleeve. At a second end of the insert on an external surface thereof there is provided a catch means. The catch means comprises a groove 102 extending about a central land 104. The central land 104 is generally wedge shaped such that a first edge 106 nearer the start of the thread extends radially less far than a second opposite edge 108 located further along the thread. A sloping surface 110 is defined between the first edge 108 and the second edge 108. Thus, when the dose dial sleeve is assembled to the insert, by threading the dose dial sleeve onto the insert, the lug 100 passes over the first edge 106 and over the sloping surface 110. As the lug 100 passes fully over the land 104 some elastic deformation of the respective elements, the dose dial sleeve and the insert occurs. Once the lug 100 is over the land 104, the second edge 105 of the land 104 acts as a stop to prevent removal of the dose dial sleeve from the insert.

The location of the second edge 108 of the land 104 is conveniently chosen at a radial location corresponding to 80 units of medicinal product, that is the maximum dose available is 80 units when the dose dial sleeve is wound from the initial position shown in any of FIG. 1, 6 or 7 to a fully extended position with the second edge 108 of the land 104 contacting the lug 100.

Figure 10:
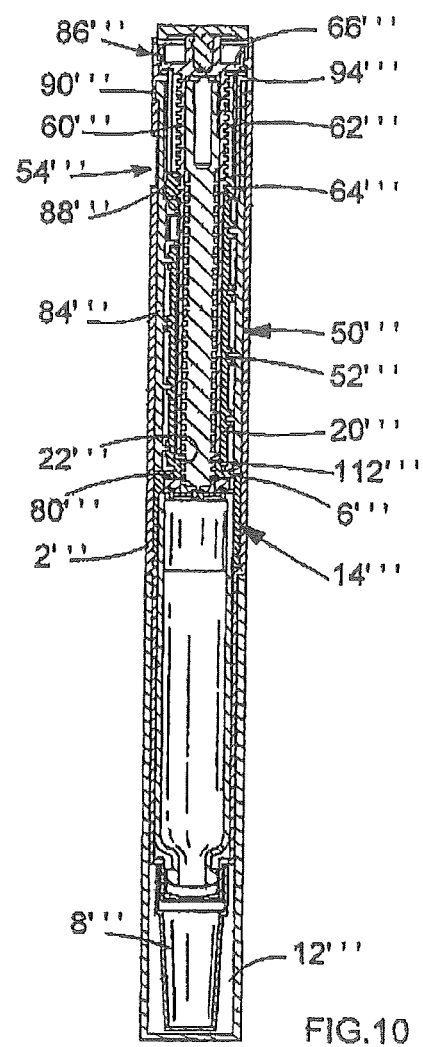
FIG. 10 shows a sectional side view of a fourth embodiment of the drug delivery device in accordance with the present invention.

A fourth embodiment of the present invention is disclosed in FIG. 10. Like reference numerals are used to refer to like parts.

As can be seen the structure of the insert 14''' has been revised. The first side of the web 6''' substantially unchanged. The other side of the web is now provided with a boss 80'''. A radial flange 112 extends outwardly from the boss 80''', the radial flange 112 being spaced from the web 6''', and a cylindrical portion 20''' extending away from the web 6''' about a periphery of the radial flange 110. A threaded opening 22''' extends through the web 6''' and the boss 80'''.

The dose dial sleeve 50''' is of modified construction. The dose dial sleeve 50'''comprises a first cylindrical portion 84''' rigidly connected to a second generally, cylindrical portion 86'''. An inner surface of the first portion 84''' and the outer surface of the cylindrical portion 20''' of the insert 14''' are provided with interengaging features to provide a helical thread 52''' between the insert 14''' and the dose dial sleeve 50'''. An outer surface of the first cylindrical portion 84'''is provided with the dose graphics. The housing 2''' is provided with an aperture or window 54''' through which a portion of the graphics may be viewed.

The second generally cylindrical portion 86''' comprises a first inner cylindrical section 88''' and a second outer cylindrical section 90'''. The first section 88''' is rigidly keyed to an inner surface of the first portion 84''' of the dose dial sleeve 50'''. The second section 90''' is preferably of the same outer diameter as the housing 2'''. Within the dose dial sleeve 50''' there is a radial flange 94 extending between the outer section 90''' and an intermediate part of the inner section 88'''.

A nut 64''' is provided on a helical thread 62''' formed on the drive sleeve 60'''. The nut 64''' is disposed between the drive sleeve 60''' and the second cylindrical section 88''' of the dose dial sleeve 50'''. The second cylindrical section 88''' and the nut 64''' are keyed together by spline means to prevent relative rotation between the nut 64''' and the dose dial sleeve 50'''.

An upper surface of the radial flange 94 of the dose dial sleeve 50''' and a step 66''' of the drive sleeve 60''' are adapted to be releasably engagable with one another to form a clutch means. When, as in FIG. 10, the dose dial sleeve 50''' and the drive sleeve 60''' are not in engagement the dose dial sleeve 50''' is able to rotate with respect to the drive sleeve 60'''. Conveniently, the clutch means comprises a plurality of radially extending longitudinally directed teeth provided respectively on the radial flange 94 of the dose dial sleeve 50''' and the step 66''' of the drive sleeve 60'''. When the dose dial sleeve 50''' and the drive sleeve 60" are not forced together the respective teeth will ride over one another.

Example 2

Figure 11:
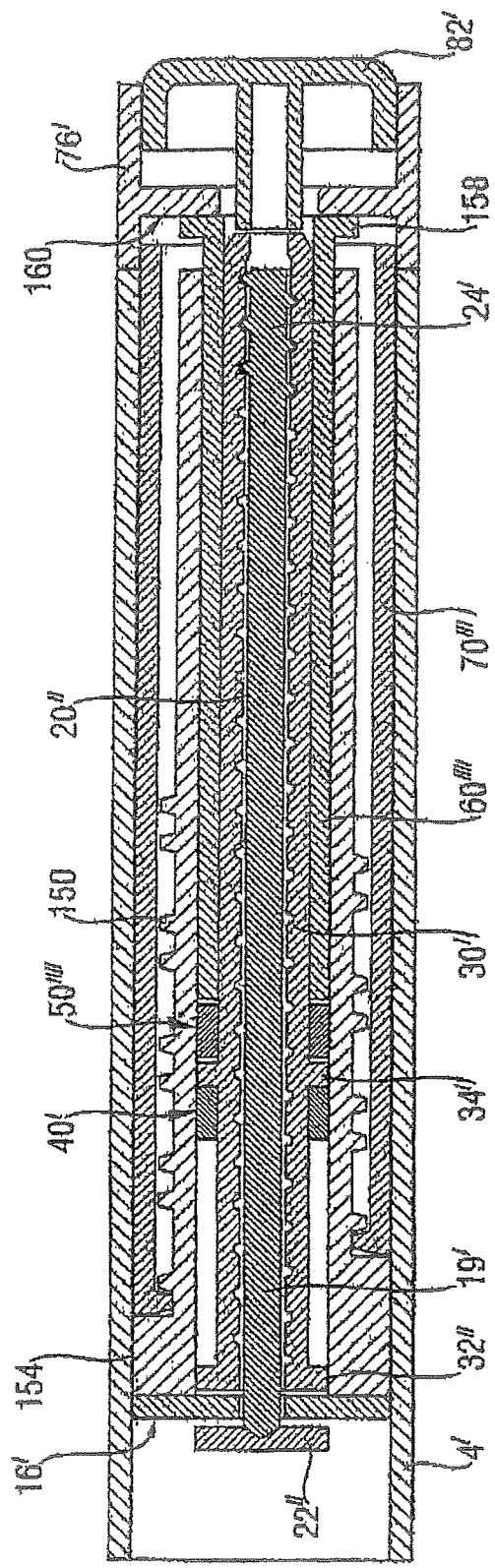
FIG. 11 shows a sectional side view of a fifth embodiment of the drive mechanism according to instant invention in a first, cartridge full, position.

In another embodiment of the invention (FIG. 11) there is seen a drive mechanism comprising a second main housing 4' having a first end and a second end. A cartridge, containing medicinal product, can be mounted to the first end of the second main housing 4' and retained by any suitable means. The cartridge and its retaining means are not shown in the illustrated embodiment. The cartridge may contain a number of doses of a medicinal product and also typically contains a displaceable piston. Displacement of the piston causes the medicinal product to be expelled from the cartridge via a needle (also not shown).

In the illustrated embodiment, an insert 16' is provided within the main housing 4'. The insert 16' is secured against rotational and axial motion with respect to the second main housing 4'. The insert 16' is provided with a threaded circular opening extending therethrough. Alternatively, the insert may be formed integrally with the second main housing 4'.

An internal housing 154 is also provided within the second main housing 4'. The internal housing 154 is secured against rotational and axial motion with respect to the second main housing 4'. The internal housing 154 is provided with a circular opening extending through its length in which a series of longitudinally 'directed splines are formed. A helical thread 150 extends along the outer cylindrical surface of the internal housing 154. Alternatively, the internal housing may be formed integrally with the second main housing 4' and/or with the insert 16'.

A first thread 19' extends from a first end of a piston rod 20". The piston rod 20" is of generally circular section. The first end of the piston rod 20" extends through the threaded opening In the insert 16' and the first thread 19' of the piston rod 20" is engaged with the thread of the insert 16'. A pressure foot 22" Is located at the first end of the piston rod 20". The pressure foot 22" is disposed to abut a cartridge piston (not shown). A second thread 24' extends from a second end of the piston rod 20". The first thread 19' and the second thread 24' are oppositely disposed.

A drive sleeve 30' extends about the piston rod 20". The drive sleeve 30' is generally cylindrical. The drive sleeve 30' is provided at a first end with a first radially extending flange 32". A second radially extending flange 34' is provided, spaced a distance along the drive sleeve 30' from the first flange 32". An external helical thread (not shown) Is provided on the outer part of the drive sleeve 30' Wending between the first flange 32" and the second flange 34'. An internal helical thread extends along the internal surface of the drive sleeve 30'. The second thread 24' of the piston rod 20" is engaged with the internal helical thread of the drive sleeve 30'.

A nut 40' is located between the drive sleeve 30' and the internal housing 154, disposed between the first flange 32" and the second flange 34' of the drive sleeve 30'. The nut 40' can be either a 'half-nut or a 'full-nut'. The nut 40' has an internal thread that is engaged with the external helical thread of the drive sleeve 30'. The outer surf-ace of the nut 40' and an internal surface of the internal housing 154 are keyed together by means of longitudinally directed splines to prevent relative rotation between the nut 40' and the internal housing 154, while allowing relative longitudinal movement therebetween.

A clicker 50"" and a clutch 60"" are disposed about the drive sleeve 30', between the drive sleeve 30' and the internal housing 154.

The clicker 50"" is located adjacent the second flange 34' of the drive sleeve 30'. The clicker 50"" includes at least one spring member (not shown). The clicker 50"" also includes a set of teeth (not shown) having a triangular profile disposed towards the second end of the drive mechanism. When compressed, the at least one spring member of the clicker 50"" applies an axial force between the flange 34' of the drive sleeve 30' and the clutch 60"". The outer surface of the clicker 50"" and an internal surface of the internal housing 164 are keyed together by means of longitudinally directed splines to prevent relative rotation between the clicker 50"" and the internal housing 154, while allowing relative longitudinal movement therebetween.

The clutch 60"" Is located adjacent the second end of the drive sleeve 30'. The clutch 60"" is generally cylindrical and is provided at its' first end with a plurality of teeth of triangular profile disposed about the circumference (not shown), that act upon the teeth of the clicker 50"". Towards the second end of the clutch 60""there is located a shoulder 158. The shoulder 158 of the clutch 60"" is disposed between the internal housing 154 and a radially inwardly directed flange of the dose dial grip 76' (described below). The shoulder 158 of the clutch 60"" is provided with a plurality of dog teeth (not shown) extending in the direction of the second end of the drive mechanism. The clutch 60"" is keyed to the drive sleeve 30' by way of splines (not shown) to prevent relative rotation between the clutch 60"" and the drive sleeve 30'.

A dose dial sleeve 70'" is provided outside of the internal housing 154 and radially inward from the second main housing 4'. A helical thread is provided on an inner surface of the dose dial sleeve 70"". The helical thread of the dose dial sleeve 70'" is engaged with the helical thread 150 of the internal housing 154.

The second main housing 4' is provided with a window (not shown) through. which part of the outer surface of the dose dial sleeve 70" may be viewed. Conveniently, a visual indication of the dose that may be dialed, for example reference numerals (not shown), is provided on the outer surface of the dose dial sleeve 70'". Conveniently, the window of the second main housing 4' allows only the dose that is currently dialed to be viewed.

A dose dial grip 76' is located towards the second end of the drive mechanism. The dose dial grip 76' is secured against rotational and axial motion within respect to the dose dial sleeve 70'". The dose dial grip 76' is provided with a radially inwardly directed flange 160. The radially inwardly directed flange 160 of the dose dial grip 76' is provided with a plurality of dog teeth (not shown) extending in the direction of the first end of the drive mechanism to abut the dog teeth of the clutch 60"". Coupling and decoupling of the dog teeth of the dose dial grip 76' with the dog teeth of the clutch 60"" provides a releasable clutch between the dose dial grip 76' and the clutch 60"".

A button 82' of generally 'T' shaped cross-section is provided at a second end of the drive mechanism. A cylindrical feature of the button 82' extends towards the first end of the drive mechanism, through an opening in the dose dial grip 76' and into a recess in the drive sleeve 30'. The cylindrical feature of the button 82' is retained for limited axial movement In the drive sleeve 30' and against rotation with respect thereto. The cylindrical feature of the button 82' has lugs extending radially (not shown) that abut the second surface of the shoulder 158 of the clutch 60"". The second end of the button 82' is generally circular and has a cylindrical skirt about its' periphery that descends towards the first end of the drive mechanism. The skirt of the button 82' is located radially inward from the dose dial grip 76'.

Operation of the drive mechanism in accordance with the present invention will now be described.

To dial a dose, a user rotates the dose dial grip 76'. The spring member of the clicker 50"" applies an axial force to the clutch 60"" in the direction of the second end of the drive mechanism. The force exerted by the spring member of the clicker 60"" couples the dog teeth of the clutch 60"" to the dog teeth of the dose dial grip 76' for rotation. As the dose dial grip 76' is rotated, the associated dose dial sleeve 70"", the drive sleeve 30' and the clutch 60"" all rotate in unison.

Audible and tactile feedback of dose being dialed is provided by the clicker 50"" and the clutch 60"". As the clutch 60"" is rotated, torque is transmitted from the teeth at the first end of the clutch 80" and the teeth of the clicker 50"". The clicker 50"" cannot rotate with respect to the internal housing 154, so the at least one spring member of the clicker 50"" deforms allowing the teeth of the clutch 60"" to jump over the teeth of the clicker 50"" producing an audible and tactile 'click'. Preferably, the teeth of the clicker 50"" and the teeth of the clutch 60"" are disposed such that each 'click' corresponds to a conventional unit of the medicinal product, or the like.

The helical thread of the dose did sleeve 70"" and the internal helical thread of the drive sleeve 30' have the same lead. This allows the dose dial sleeve 70'" to advance along the thread 150 of the internal housing 154 at the some rate as the drive sleeve 30' advances along the second thread 24' of the piston rod 20".

Rotation of the piston rod 20" is prevented due to the opposing direction of the first thread 19' and the second thread 24' of the piston rod 20". The first thread 19' of the piston rod 20" is engaged with the thread of the insert 16' and so the piston rod 20" does not move with respect to the second main housing 4' while a dose is dialed.

The nut 40', keyed to the internal housing 154, is advanced along the external thread of the drive sleeve 30' by the rotation of the drive sleeve 30'. When a user has dialed a quantity of medicinal product that is equivalent to the deliverable volume of the cartridge, the nut 40' reaches a position where it abuts the second flange 34' of the drive sleeve 30'. A radial stop formed on the second surface of the nut 40' contacts a radial stop on the first surface of the second flange 34' of the drive sleeve 30', preventing both the nut 40' and the drive sleeve 30' from being rotated further.

Should a user inadvertently dial a quantity greater than the desired dosage, the drive mechanism allows the dosage to be corrected without dispense of medicinal product from the cartridge. The dose dial grip 78' is counter-rotated. This causes the system to act in reverse. The torque transmitted through the clutch 60"" causes the teeth at the first end of the clutch 60"" to ride over the teeth of the clicker 50"" to create the clicks corresponding to the dialed dose reduction.

When the desired dose has been dialed, the user may then dispense this dose by depressing the button 82' In the direction of the first end of the drive mechanism. The lugs of the button 82' apply pressure to the second surface of the shoulder 158 of the clutch 60"", displacing the clutch 60"" axially with respect to the dose dial grip 76'. This causes the dog teeth on the shoulder 168 of the clutch 60"" to disengage from the dog teeth of the dose dial grip 76'. However, the clutch 60"" remains keyed in rotation to the drive sleeve 30'. The dose dial grip 76' and associated dose dial sleeve 70'" are now free to rotate (guided by the helical thread 150 of the internal housing 154).

The axial movement of the clutch 60"" deforms the spring member of the clicker 50" and couples the teeth at the first and of the clutch 60" to the teeth of the clicker 50" preventing relative rotation therebetween. This prevents the drive sleeve 30' from rotating with respect to the internal housing 154, though it is still free to move axially with respect thereto.

Pressure applied to the button 82' thus causes the dose dial grip 76' and the associated dose dial sleeve 70'" to rotate into the second main housing 4'. Under this pressure the clutch 60"", the clicker 50"" and the drive sleeve 30' are moved axially In the direction of the first end of the drive mechanism, but they do not rotate. The axial movement of the drive sleeve 30' causes the piston rod 20" to rotate through the threaded opening In the insert 16', thereby to advance the pressure foot 22". This applies force to the piston, causing the medicinal product to be expelled from the cartridge. The selected dose is delivered when the dose dial grip 76' returns to a position where It abuts the second main housing 4'.

When pressure Is removed from the button 82', the deformation of the spring member of the clicker 50"" is used to urge the clutch 60"" back along the drive sleeve 30' to re-couple the dog teeth on the shoulder 158 of the clutch 60"" with the dog teeth on the dose dial grip 76'. The drive mechanism is thus reset in preparation to dial a subsequent dose.

The invention claimed is:

1. An injector comprising:
    a cartridge holder;
    an exterior housing connected to the cartridge holder and enclosing a dose setting and delivery mechanism comprising,
    a non-circular cross section piston rod;
    a dose dial sleeve;
    a nut having external splines;
    a unidirectional coupling,
    the injector further comprising a dose dial grip axially fixed to a distal end of the exterior housing, where the dose dial grip rotates relative to the exterior housing and is in a clutched engagement with a drive sleeve such that during dose setting the drive sleeve and dose dial grip are rotationally fixed,
    wherein the unidirectional coupling allows movement of the piston rod in proximal direction and prevents movement of the piston rod in the distal direction during dose setting.

2. The injector of claim 1 further comprising a dose button positioned within and extending through the dose dial grip such that axial movement in a proximal direction when a dose is set will cause the clutched engagement to disengage such that the drive sleeve can rotate relative to the dose dial grip.

3. The injector of claim 1 where the nut moves axially in a distal direction to an axial position each time a dose is set, where the axial position of the nut corresponds to an amount of medicinal product remaining in the injector.

4. The injector of claim 3 where axial movement of the nut is a result of the nut rotating relative to the exterior housing and where rotation of the nut is prevented if during a setting of a desired dose a quantity of medicinal product remaining in the injector is less than the desired dose.

5. The injector of claim 1 where the dose dial grip rotates in a first direction during dose setting and can counter-rotate in a second direction to cancel a set dose without movement of the piston rod.

6. The injector of claim 5 where counter-rotation of the dose dial grip in the second direction causes audible clicks that correspond to the set dose.

7. The injector of claim 1 further comprising a stored energy drive mechanism configured for use in dose delivery to drive the drive sleeve causing the piston rod to rotate.

8. The injector of claim 7 where the stored energy drive mechanism is a spring.

9. The injector of claim 1 further comprising a clicker associated with the drive sleeve and configured to cause a series of audible and tactile clicks upon dose setting and dose delivery.

10. The injector of claim 1 further characterized in that the unidirectional coupling is configured to prevent rotation of the piston rod during dose setting and to allow the piston rod to rotate during dose delivery.

\* \* \* \* \*

UNITED STATES PATENT AND TRADEMARK OFFICE
CERTIFICATE OF CORRECTION

PATENT NO. : 10,226,579 B2  
APPLICATION NO. : 15/352893  
DATED : March 12, 2019  
INVENTOR(S) : Robert Frederick Veasey, Christopher Nigel Langley and Steven Wimpenny Page 1 of 1

It is certified that error appears in the above-identified patent and that said Letters Patent is hereby corrected as shown below:

On the Title Page

Column 1 (Related U.S. Application Data), Line 2, delete "8,873,782," and insert -- 8,876,782, --, In the Specification In Column 1, Line 3, above "THE TECHNICAL FIELD OF THE INVENTION" insert -- The present application is a continuation of U.S. application Ser. No. 14/504,016, filed Oct. 1, 2014, which is a continuation of U.S. application Ser. No. 13/667,449, filed Nov. 2, 2012, now U.S. Pat. No. 8,876,782, which is a continuation of U.S. application Ser. No. 13/280,903 filed Oct. 25, 2011, now U.S. Pat. No. 8,574,198, which is a continuation of U.S. application Ser. No. 12/453,626 filed May 15, 2009, now U.S. Pat. No. 8,070,727, which is a continuation of U.S. application Ser. No. 10/790,024 filed Mar. 2, 2004, now U.S. Pat. No. 7,553,299, which claims priority to GB Patent Application No. 0304823.8, filed on Mar. 3, 2003. The entire disclosure contents of these applications are herewith incorporated by reference into the present application. --.

Signed and Sealed this  
Fourteenth Day of May, 2019

Andrei Iancu  
*Director of the United States Patent and Trademark Office*